(12) United States Patent
Averill et al.

(10) Patent No.: US 6,802,203 B1
(45) Date of Patent: Oct. 12, 2004

(54) ROTARY SEAL TESTING MACHINE

(75) Inventors: Bryan M. Averill, Portland, OR (US); Nathan W. Butler, Portland, OR (US); Oliver Heravi, Portland, OR (US); Scott J. Pugliese, Portland, OR (US)

(73) Assignee: Warn Industries, Clackamas, OR (US)

( * ) Notice: Subject to any disclaimer, the term of this patent is extended or adjusted under 35 U.S.C. 154(b) by 0 days.

(21) Appl. No.: 10/198,975

(22) Filed: Jul. 18, 2002

(51) Int. Cl.[7] ............................. G01N 3/56; F16J 15/00; G01M 3/04

(52) U.S. Cl. .................. 73/9; 277/320; 73/46; 73/49.8

(58) Field of Search .............................. 73/9, 49.8, 46, 73/7, 10, 47; 277/320

(56) References Cited

U.S. PATENT DOCUMENTS

| | | | |
|---|---|---|---|
| 1,520,939 A | * | 12/1924 | Dorer .......................... 277/320 |
| 3,180,135 A | | 4/1965 | Cain, Jr. et al. |
| 3,313,141 A | | 4/1967 | Jagger et al. |
| 3,362,213 A | * | 1/1968 | Van Deven et al. ............. 73/9 |
| 3,589,737 A | * | 6/1971 | Sedy ........................... 277/320 |
| 3,987,663 A | | 10/1976 | Repella |
| 4,749,898 A | | 6/1988 | Suzuki et al. |
| 4,750,360 A | | 6/1988 | Smith |
| 5,074,568 A | * | 12/1991 | Bertsch ....................... 277/320 |
| 5,239,864 A | | 8/1993 | von Pragenau |
| 5,575,176 A | | 11/1996 | Rohrs et al. |
| 5,628,516 A | * | 5/1997 | Grenke ........................ 277/320 |
| 5,755,372 A | * | 5/1998 | Cimbura, Sr. ................ 277/320 |
| 5,814,717 A | | 9/1998 | Antonini et al. |
| 6,276,194 B1 | | 8/2001 | Vinton et al. |

FOREIGN PATENT DOCUMENTS

JP 06050439 A * 2/1994 .................. 277/320

* cited by examiner

*Primary Examiner*—Michael Cygan
(74) *Attorney, Agent, or Firm*—Harness, Dickey & Pierce, P.L.C.

(57) ABSTRACT

A rotary seal machine is provided and includes a motor drive shaft which extends into and through a canister. A test seal specimen surrounds the shaft in the outer wall, and contaminant circulates through the canister for inducing leakage of the contaminant through the seal being tested. The seal and protruded shaft are visually exposed from outside the outer wall so that contaminant leakage past the seal can be visually detected.

7 Claims, 5 Drawing Sheets

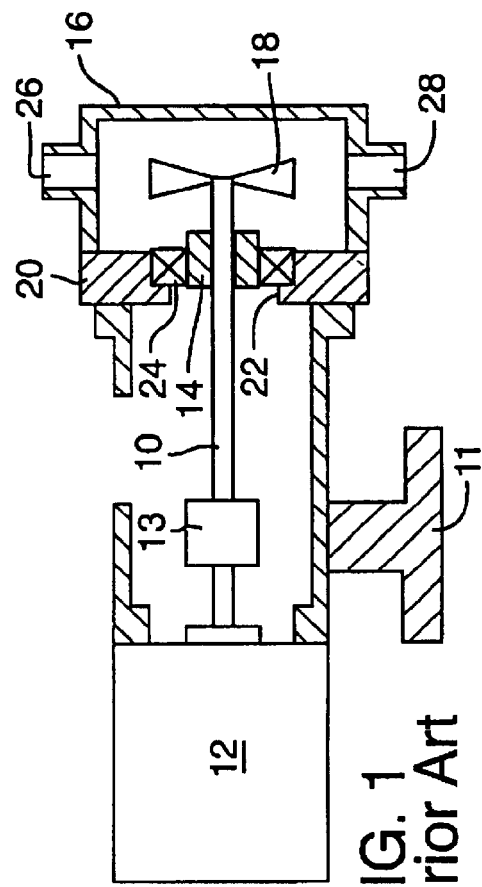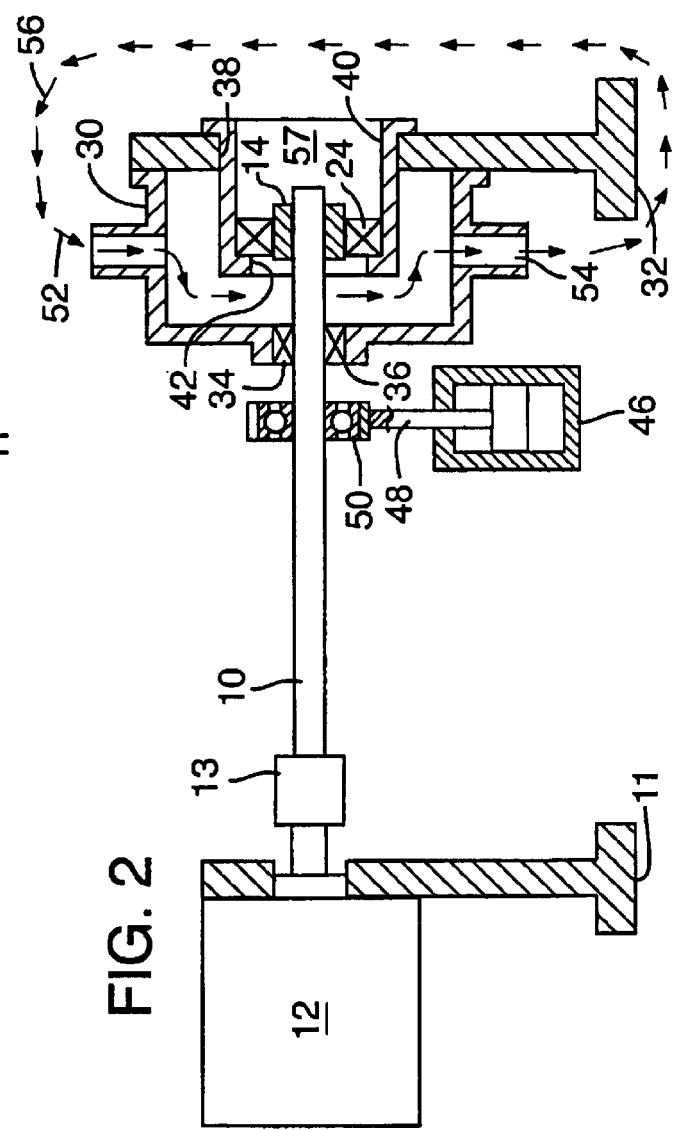
FIG. 1 Prior Art
FIG. 2

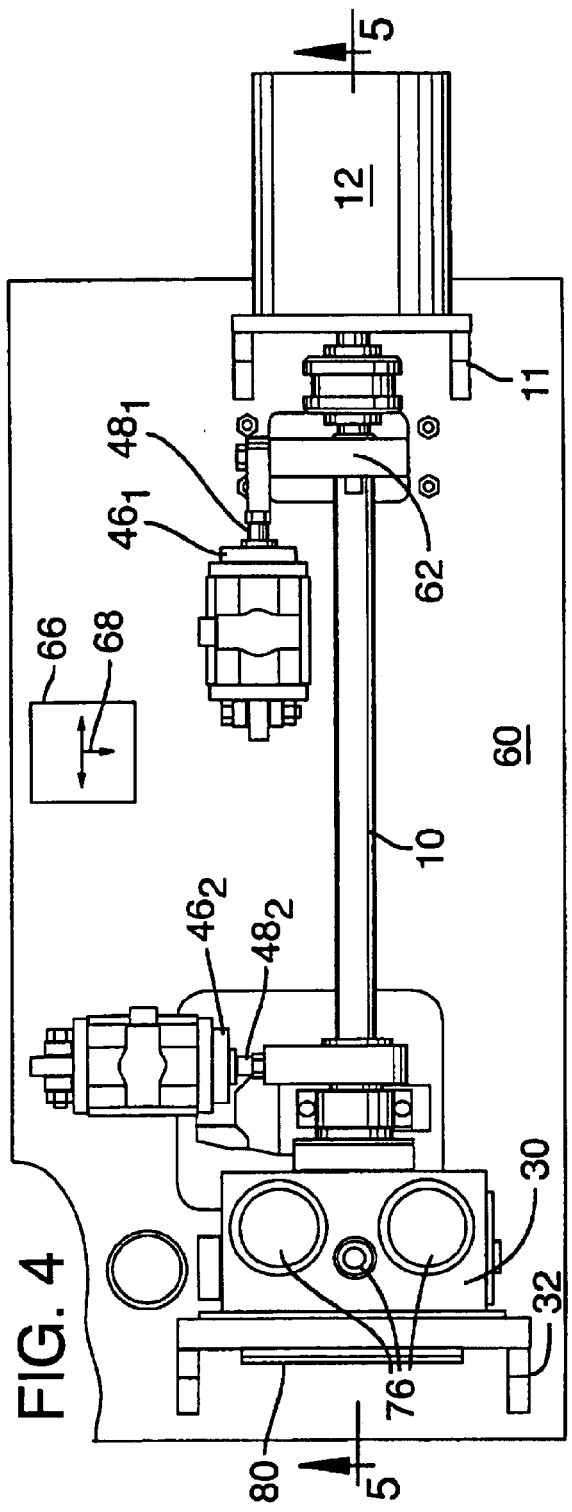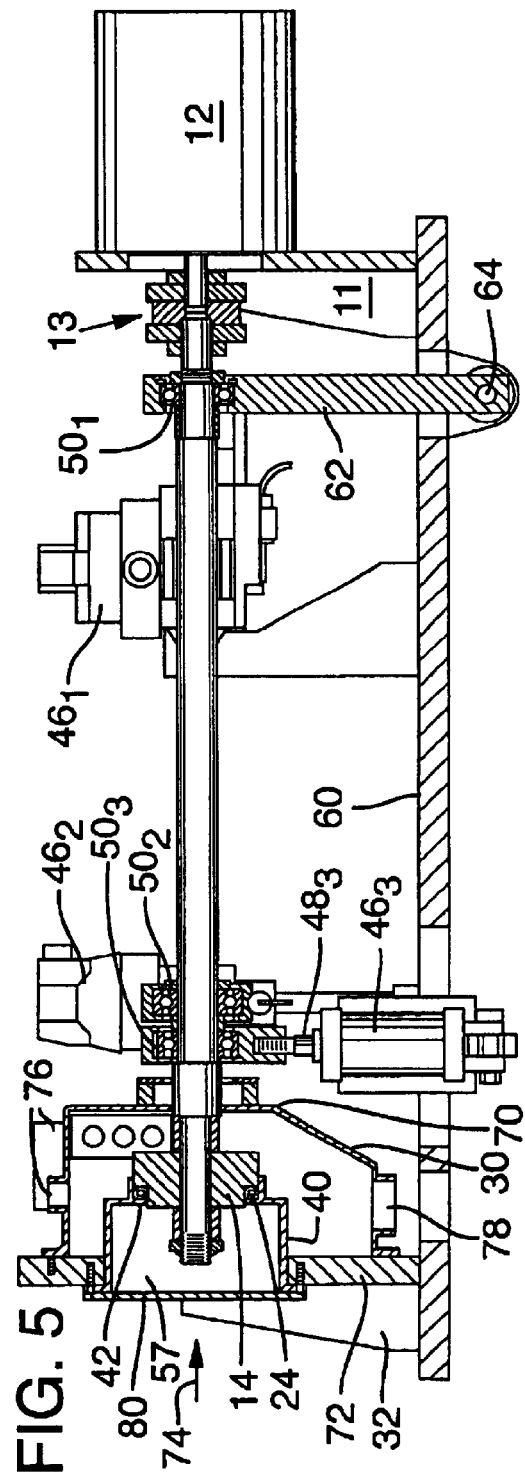

ROTARY SEAL TESTING MACHINE

FIELD OF THE INVENTION

This invention relates to a machine for testing the sealing capabilities of rotary seals, e.g., seals provided to seal between a rotating shaft and a surrounding non-rotating wall, sleeve, housing, etc.

BACKGROUND OF THE INVENTION

Rotary seals as contemplated herein are used when a rotating shaft extends through a non-rotating member, e.g., the wall of a housing into which the shaft is extended and wherein a clean environment is to be maintained as compared to a dirty environment outside the housing. An example is the drive line of a four-wheel drive vehicle. The drive line extends from an engine, into and through a transmission and transfer case, to and through front and rear differentials and to the front and rear wheels, i.e. via the front and rear axles. At each of these junctures, drive and driven shafts are interconnected to other drive and driven shafts with various forms of mechanical devices that change drive direction, change gears, connect and disconnect the drive and driven shafts, etc. In each case there is a housing that surrounds the mechanism, bearings that support the mechanism, and one or more rotating shafts projecting into and out of the housing. The drive line is located under the vehicle body and adjacent a roadway where all manner of contaminants (dust, water, mud, snow, exhaust, etc.) make up the outside environment. Leakage of these contaminants into the housing will have a deleterious affect on the mechanical devices and bearings within the housing.

Furthermore the drive line of a four-wheel-drive vehicle is subjected to the hardships inherent when driving the vehicle off-road. The wheel ends of the front and rear axles in particular are subjected to jarring and twisting as the wheels encounter typical off-road surface anomalies such as ruts, rocks, and stream beds. Also, the environment at the wheel ends is the dirtiest as the wheels kick up whatever is present in the off-road environment. A shift mechanism contained in the wheel end whereat, e.g., the front wheels are shifted between two-wheel and four-wheel drive, need to be protected from the outside environment. This is the task of the rotary seal surrounding the drive axle which is projected through a housing and into the shift mechanism at the wheel end. Whereas the invention is applicable not only to other positions in the drive line but to other rotating shaft applications as well, the embodiments here disclosed are directed to the conditions found at the wheel end of a four-wheel-drive vehicle, by way of example only.

Schematically illustrated in FIG. 1 of the drawings is a seal test apparatus of the prior art which is supported on a machine base 11. A shaft 10 is shown mounted to a motor 12. The shaft 10 extends into a canister 16 also supported by the machine base 11. The interior of the canister 16 contains contaminant which represents the outside or dirty environment to which the axle of a vehicle is exposed. (A paddle 18 agitates the contaminant in the canister to insure exposure of the contaminant to the seal being tested.) A seal housing adapter 20 and a shaft adapter 14 are constructed for the test apparatus to duplicate the configuration of the opening 22 through which the shaft 10 will be directed in real life. A seal specimen 24 designed for the opening 22 is fitted to the adapter 20 and the seal 24 is ready to be tested. A fill opening 26 is provided in the canister to input a variety of contaminants and as each contaminant test is completed, the contaminant is drained through drain opening 28 and the canister is refilled with a different contaminant sample.

As illustrated, the test results are determined by viewing or testing leakage through the seal specimen 24 at the inner side of the canister, i.e., between the canister and the motor. Such viewing is severely restricted and unsatisfactory. Also, the test program itself does not adequately represent the stresses to which the seals are subjected in real life.

BRIEF DESCRIPTION OF THE INVENTION

In the present invention, the test shaft is projected into the canister at the inner wall and continues to be projected through an outer wall formed in part by a housing adapter. A shaft adapter and seal specimen are mounted in the housing adapter. Placement of the seal in the outer wall allows the seal to be directly examined during testing, i.e., they can be viewed straight on from the outer side of the canister. At the inner side, a computer controlled actuator or actuators are mounted to the test shaft. The computer is programmed with information obtained, e.g., at a vehicle test site where sensors installed on a vehicle gather and record the accelerations, displacements, and rpm imposed onto a vehicle axle as the vehicle is driven over a prescribed test route designed to accelerate vehicle wear. The contaminants are circulated through the canister rather than batch filled to the canister. The test results are more easily obtained and the test program itself more accurately represents the wheel end of a vehicle being driven in actual accelerated test conditions.

The invention will be more clearly understood upon reference to the following detailed description and accompanying drawings.

DETAILED DESCRIPTION OF THE DRAWINGS

FIG. 1 is a schematic illustration of a rotary seal testing machine representing the prior art;

FIG. 2 is a schematic illustration of a rotary seal testing machine representing the present invention;

FIG. 4 is a top view of the preferred embodiment of FIG. 3;

FIG. 5 is a section view taken on section lines 5—5 of FIG. 4;

DETAILED DESCRIPTION OF THE PREFERRED EMBODIMENT

Figure 3:
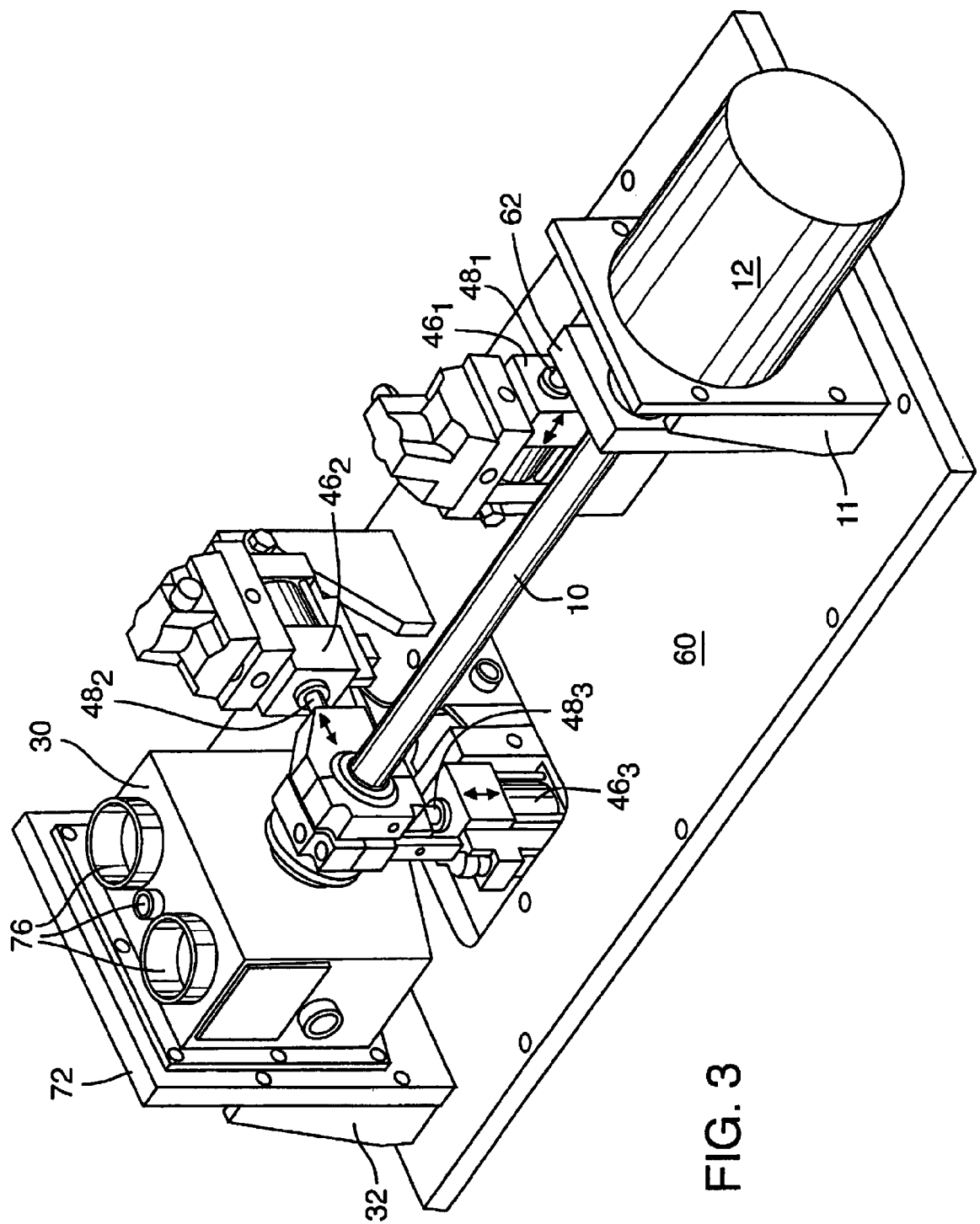
FIG. 3 is a pictorial view of a preferred embodiment of the present invention.

The preferred embodiment of the invention will be first explained in general having reference to the schematic illustration of FIG. 2. In FIG. 2 a motor 12 is supported on a machine base 11 and rotatably drives a test shaft 10 having a flex coupling 13 that couples the shaft 10 to the output shaft of motor 12. A canister 30 is supported on its own base 32 and is provided with a receiving bore 36 fitted with a canister seal 34. A seal housing adapter 40 is specifically designed to fit opening 38 of canister support base 32 and to produce an opening 42 configured to duplicate the real life opening, e.g., in a wheel end housing for receiving an axle. The shaft 10 is extended through the canister seal 34 and further extended through the opposing wall of the canister provided by opening 42. A seal specimen 24 is fitted to the opening 42 and surrounds the axle. A shaft adapter 14 is fitted to the shaft 10 and represents the axle configuration of the real life axle that will extend through the rotary seal 24.

Fitted to the shaft 10 at a position between the motor 12 and canister 30 is an actuator 46 having a plunger 48 acting against a spherical bearing 50 surrounding the shaft 10. Although not shown in FIG. 2, a computer controls the actuator and produces vertical motion to the shaft for simulating that experienced in driving a vehicle. Preferably a second laterally positioned actuator and spherical bearing are provided to produce the simulated motion in a horizontal direction in addition to or instead of the vertical actuator, and a third actuator may be provided to simulate motion along the axis of the shaft. All are connected to the shaft with spherical bearings and are preferably computer controlled as illustrated and described in connection with the hereafter description of the preferred embodiment.

A fill inlet 52 is provided at the top of the canister 30 and a drain outlet 54 is provided at the bottom of the canister. Although the illustrated design can readily be equipped with an agitator, and batch filled with contaminant material as described for FIG. 1, preferably the contaminant is circulated as illustrated by arrows 56. When a different contaminant is desired for testing, the flow of contaminant (arrows 56) is interrupted to bleed off the old and insert a new contaminant with little or no interruption in the test program.

Most importantly is the exposure of the seal specimen 24 at the outer side of the canister. Whereas an inset or cavity 57 is formed by the seal housing adapter 40, a transparent face plate or cover may be provided across the opening into the cavity to capture and contain any contaminant that leaks past the rotary seal specimen 24 into the cavity. Such permits collection and testing of the leaked contaminant.

It will be appreciated that when viewing the rotary seal 24 from the outer side, e.g., through the face plate, one is looking at the seal from what it's position would be inside the enclosure whereat the shift mechanism resides at the wheel end of a vehicle. Whatever leakage of contaminant occurs through the seal and into the cavity 57 is what the shift mechanism would be exposed to. This occurs in part because the adapter 14 represents the true seating of an axle in the rotary seal, the axle being subject to the same dynamics and environmental conditions as occurs in real driving, i.e., as generated by the actuator(s) 46, the drive motor 12, and the contamination circulation system 56.

Reference is now made to FIGS. 3–6. As shown in the figures, the components of the machine are mounted to a table top 60. The motor support 11 is anchored to the table top 60 and supports the motor 12. As shown, the motor 12 rotatably drives the shaft 10 which includes flex coupling 13 (see FIG. 5). The shaft 10 extends through a first spherical bearing $50_1$. A lever 62 is pivoted at pivot point 64 just below table top 60 and extends upwardly through the table top to a position above the shaft 10. The shaft extends through an opening in the lever 62 and the bearing $50_1$, is fitted to the lever at said opening. An actuator $46_1$, having a plunger $48_1$, is connected to the lever 62. As noted in FIG. 4, the plunger $48_1$, is moved parallel to the shaft 10 by the actuator to pivot the lever and thereby produce axial movement of the axle 10.

The shaft 10 extends from its coupling with lever 62 to a second spherical bearing $50_2$. Bearing $50_2$ is coupled to a second actuator $46_2$ having a plunger $48_2$ that produces linear motion to the shaft normal to the axis of shaft 10 and in a horizontal direction. Following spherical bearing $50_2$ is a third spherical bearing $50_3$ which is connected to a plunger $48_3$ of a third actuator $46_3$. This latter actuator $46_3$ produces movement normal to the axis of the shaft in a vertical direction.

As previously mentioned, the three actuators 46 are intended to simulate the accelerations and displacements applied to a wheel axle as experienced by a vehicle when driving over a prescribed test route. These accelerations and displacements are determined using test equipment which record the data while a vehicle is driven in accelerated real life conditions, e.g., at a vehicle test site. The data are analyzed and programmed into a computer. The computer is schematically illustrated as reference 66 in FIG. 4 having connections to the actuators 46 indicated by arrows 68. The computer coordinates the plunger movement of the three actuators to reproduce the actual vehicle test conditions.

Figure 7:
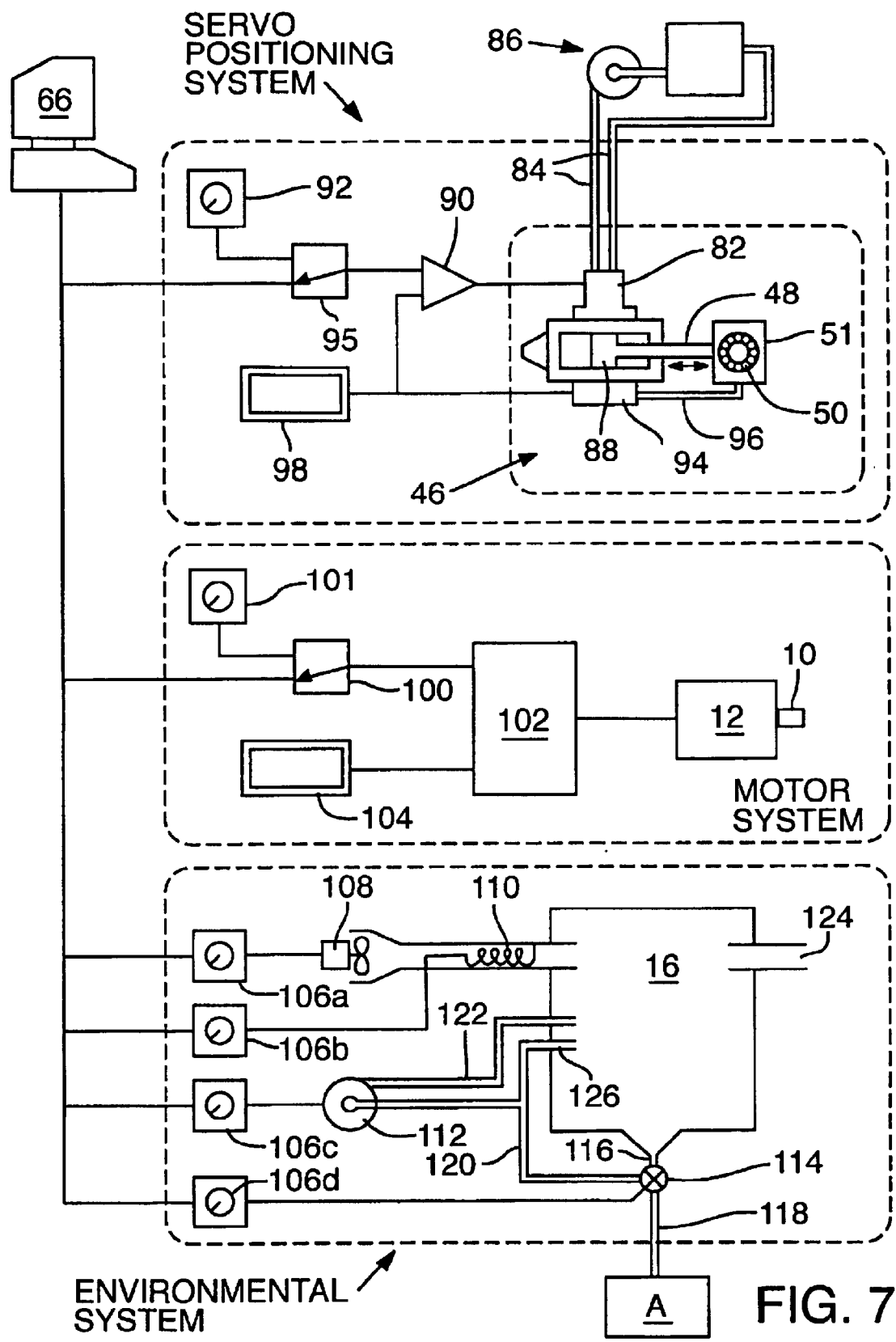
FIG. 7 schematically illustrates operating systems for operating the test apparatus of FIGS. 3–6.

Preferred systems for computer control of the machine operations are schematically illustrated in FIG. 7. Each of the actuators $46_1$, $46_2$ and $46_3$ has a separate but similar servo positioning system, i.e., there are three similar servo positioning systems but each is independently controlled by the same computer 66. FIG. 7 illustrates one actuator and its servo positioning system but is representative of the systems of all three actuators.

As noted in FIG. 7, an actuator 46 is shown including a plunger or rod 48 connected to a rod end fitting 51 which contains a bearing 50. The actuator assembly includes a servo valve 82 which controls the input/output of hydraulic fluid through lines 84 to and from a hydraulic power supply 86. Accordingly hydraulic fluid is pumped to and from the inner and outer sides of the piston 88 to produce movement of the bearing 50 (and thus shaft 10), such movement being back and forth in a lateral direction as illustrated in FIG. 7.

The servo valve 82 receives its instructions from a servo amplifier 90 and the servo amplifier 90 obtains its instructions from either the computer 66 or from a manual control 92. A selector switch 95 is set for the desired control source, i.e., manual control 92 or computer control 66. As illustrated, the computer 66 is controlling the actuator in the illustration of FIG. 7 and it reproduces the recorded real life movements obtained from a road test. It will be appreciated that all three actuators (or whatever number of actuators) are individually and cooperatively controlled by the computer 66 (or alternatively manual control 92) to generate the real life experience recorded in the field. The control of the single actuator of FIG. 7 is but one component of such movements.

The manner of control is a standard closed circuit transducer and those skilled in the art will recognize that whereas the computer (or manual control) is instructing the servo amplifier 90 as to the desired movement, the servo amplifier is receiving information also from the displacement transducer 94 as to the movement presently being generated by the servo valve 82. The servo amplifier monitors the two inputs (e.g., from the computer and transducer) and whatever the difference, signals the servo valve 82 to increase or decrease movement rate and/or distance of movement until the signal from the displacement transducer verifies that the desired movement is achieved. The displacement transducer 94 determines the lateral movement of bearing 50, e.g., via a probe 96. A monitor 98 receives the information from the displacement transducer as discussed to enable an operator to visually monitor the resultant movement imposed onto the shaft.

The motor system is also illustrated in FIG. 7. A selector switch 100 provides selective control by either the computer 66 or manual control 101. Whichever control is selected, that control is connected to a motor controller 102 which in turn controls the main motor 12 (which rotates shaft 10). A display 104 connected to the controller 102 displays the RPM of shaft 10.

Returning to the illustrations of FIGS. 3–6, following the three positions of spherical bearing connection to the three actuators 46, the shaft 10 extends into and through canister 30 and terminates in the cavity 57 formed in outer wall 72. Forming a part of the outer wall 72 of canister 30 is a customized seal housing adapter 40 defining an opening 42. This opening through adapter 40 is specifically configured to simulate the opening in a housing, e.g., a wheel end housing occupied by a coupling mechanism for shifting a vehicle between, e.g., two-wheel drive and four-wheel drive. The reader should understand that the outer side of the opening 42 is that configuration that resides inside the wheel end housing in real life. A shaft adapter 14 is custom produced to simulate the axle that projects through the wheel end housing (in real life) and thus the seating of the seal specimen 24 represents the actual seating of the seal in real life conditions so that as viewed from the outer side (see arrow 74 in FIG. 5), leakage that is detected passing from inside the canister to the outer side is the leakage that will be experienced in real life, i.e., passing through seal 24 and into the wheel end housing, i.e., whereat the coupling mechanism resides.

The canister 30 is provided with inlet openings 76 (one or two of which may be closed off) for inputting contaminants of whatever kind and type to which the seals 24 may be exposed in real life. Outlet opening 78 enables draining or recirculation of the contaminants, the recirculation being illustrated in FIG. 2 by arrows 56. As previously explained for FIG. 2, the configuration of the canister 30 is such that a cavity 57 is formed. The exterior or outer side of the cavity (the seal 24 located in the cavity) is provided with a removable, transparent cover 80.

Figure 6:
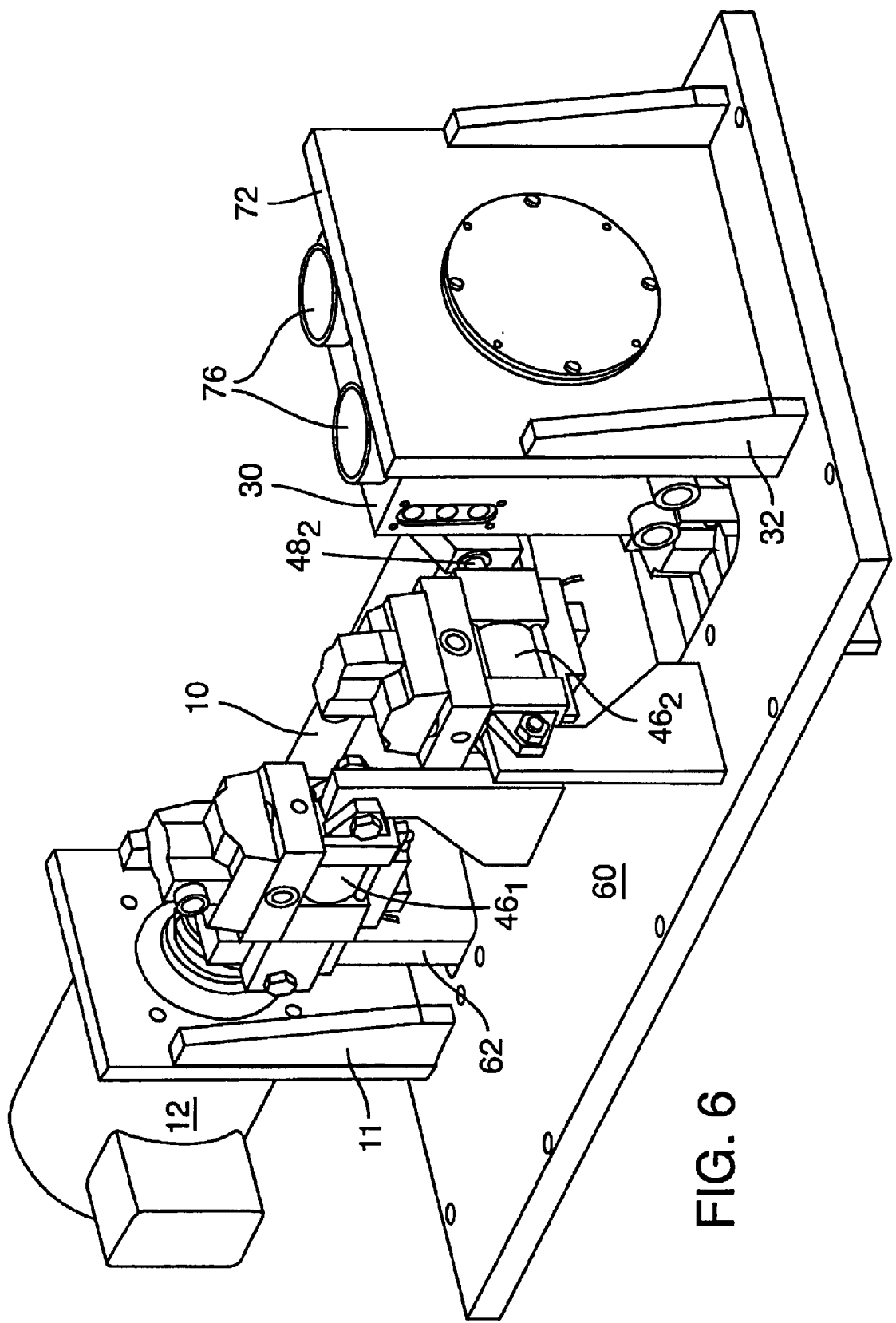
FIG. 6 is a pictorial view as viewed from the opposite end of that shown in FIG. 3.

In operation, a shaft adapter 14 and a housing adapter 40 are structured to fit the shaft 10 and canister housing outer wall 72 while cooperatively defining the envelope configuration for the specific application of the rotary seal to be tested. The adapters and seal specimen are assembled to the shaft 10 and canister 30 to provide what is intended to be an air tight canister interior. Contaminants are cycled into and through the canister in a manner that simulates the contaminants of actual vehicle test conditions. The actuators are actuated under the control of the computer 66 (FIG. 4) and the test operator is able to view the effectiveness of the rotary seal through the window/transparent cover plate 80 (FIG. 6). Further, the test operator is able to collect deposits of contaminants as desired by removing the cover and obtaining samples of the deposits, e.g., as may be deposited on a removable cavity liner.

The environmental system is preferably also computer controlled and an example is shown in FIG. 7. As noted, a line from computer 66 extends to the environmental system. The primary line of connection is split into four lines, each connected to a manual override control 106A, 106B, 106C and 106D. 106A as noted is connected to blower 108, 106B is connected to heater 110, 106C is connected to pump 112 and 106D is connected to valve 114.

The temperature inside the canister 16 is established through activation of the heater 110 and blower 108. Although not illustrated, the reader will appreciate that the temperature may be lowered as well as raised, e.g., employment of liquid nitrogen or cooling coils. The contaminants are delivered to the canister 16 via the pump 112. The computer 66 (or override control 106D) directs valve 114 to close drain line 116 and open delivery line 118 thereby connecting contaminant A to line 120 (via valve 114) which contaminant is pumped through delivery line 122 and into the canister 16. When the desired contaminant is pumped into the canister, the valve 114 is closed to line 118 and open to drain line 116. The contaminant A is thus circulated from drain line 116 and back into the canister. Such control may be effected by positive or negative pressure applied within the canister 16 and/or within the cavity 57. An exhaust 124 is provided to control pressurization of the canister. An over flow return line 126 may be provided to prevent over filling of the canister with, e.g., liquid contaminant. When the test for contaminant A is completed, valve 114 will connect line 116 to line 18 and deliver the contaminant to its storage (A).

The reader will appreciate that the exposure of contaminant A to the seal specimen 24 is controlled by the circulation of the contaminant through the system and that the type of contaminant may be varied by interconnecting multiple of contaminants (B, C, D, etc.) through further valves that selectively connect the different contaminants to line 120 via valve 114 as discussed above. The reader should further understand that as particularly relates to the environmental system of FIG. 7, this system may be devised in may different ways as will be known to those skilled in such art. The illustration of FIG. 7 is symbolic in nature and is not intended to indicate uniqueness but rather to provide an understanding of the overall setting within which the invention is embodied.

Whereas the preferred embodiment is described and illustrated, those skilled in the art will readily conceive of numerous variations and modifications without departing from the scope intended for the invention. The primary objective of the invention is the improved access to the seal during testing. The structure of the invention essentially places the viewer inside the wheel end housing and enables real time detection of the effectiveness of the seal. Further, the actuators are established to provide real life simulation of the rigors to be experienced by the rotary seal under actual driving conditions. The inside/outside viewing is believed to be a major benefit and is achieved by passing the test shaft into and through the canister whereby the seal specimen can be located at the exposed outer wall. The intended scope of the invention will be appreciated by reference to the claims, the terms of which are intended to be given the meaning that is common to the industry.

What is claimed is:

1. A rotary seal test machine comprising:
   a motor;
   a test shaft driven by the motor;
   a canister defining an enclosure and having inner and outer side walls with opposing and aligned inner wall and outer wall bores;
   said test shaft extended from said motor and into the canister through said inner wall bore;
   a housing adapter fitted to said outer wall bore and defining a secondary bore configured to duplicate a bore in which a defined seal specimen is to provide a sealing engagement surrounding a defined rotary shaft;
   said test shaft extended through said secondary bore and at the point of being extended through said secondary bore provided with a circumferential configuration simulating said defined rotary shaft, and said defined seal specimen surrounding said circumferential configuration;
   a contaminant contained in the canister enclosure and directed onto said shaft and seal specimen within said enclosure, said shaft protruded through said outer wall exposed for detection of contaminants leaking past the seal; and an actuator assembly connected directly to the shaft and actively imparting controlled displacements to the shaft to simulate changes in axial and lateral displacements applied to said defined shaft during operation of said rotary seal test machine.

2. A rotary seal test machine as defined in claim 1 wherein the canister is provided with an inlet and an outlet, said contaminant being circulated into and through the canister.

3. A rotary seal test machine as defined in claim 1 wherein the secondary bore as defined by said housing adapter is inset from the outer wall bore and defines an inset cavity, and a transparent cover affixed over said cavity to entrap contaminant that leaks past the seal specimen while permitting operator viewing of the cavity.

4. A rotary seal test machine comprising:

a motor;

a test shaft driven by the motor;

a canister defining an enclosure and having inner and outer side walls with opposing and aligned inner wall and outer wall bores;

said test shaft extended from said motor and into the canister through said inner wall bore;

a housing adapter fitted to said outer wall bore and defining a secondary bore configured to duplicate a bore in which a defined seal specimen is to provide a sealing engagement surrounding a defined rotary shaft;

said test shaft extended through said secondary bore and at the point of being extended through said secondary bore provided with a circumferential configuration simulating said defined rotary shaft, and said defined seal specimen surrounding said circumferential configuration;

a contaminant contained in the canister enclosure and directed onto said shaft and seal specimen within said enclosure, said shaft protruded through said outer wall exposed for detection of contaminants leaking past the seal;

an actuator assembly connected to the shaft and imparting linear motion to the shaft to simulate motions applied to said defined shaft; and wherein said linear motion of said actuator assembly includes a piston connected to a spherical bearing, the bearing secured to the test shaft.

5. A rotary seal test machine comprising:

a motor;

a test shaft driven by the motor;

a canister defining an enclosure and having inner and outer side walls with opposing and aligned inner wall and outer wall bores;

said test shaft extended from said motor and into the canister through said inner wall bore;

a housing adapter fitted to said outer wall bore and defining a secondary bore configured to duplicate a bore in which a defined seal specimen is to provide a sealing engagement surrounding a defined rotary shaft;

said test shaft extended through said secondary bore and at the point of being extended through said secondary bore provided with a circumferential configuration simulating said defined rotary shaft, and said defined seal specimen surrounding said circumferential configuration;

a contaminant contained in the canister enclosure and directed onto said shaft and seal specimen within said enclosure, said shaft protruded through said outer wall exposed for detection of contaminants leaking past the seal;

an actuator assembly connected to the shaft and imparting linear motion to the shaft to simulate motions applied to said defined shaft;

wherein the shaft defines an axis and the actuator assembly applies linear motion perpendicular to the axis of the shaft;

wherein the actuator assembly also applies linear motion along the axis of the shaft; and wherein multiple actuators include multiple pistons applying multiple directions of motion, all directed to the test shaft through spherical bearings.

6. A rotary seal test machine comprising:

a motor;

a shaft driven by the motor;

a canister defining an enclosure and having first and second side walls, at least one of said first and second side walls including an opening therein;

said shaft extending from said motor and into the canister through said opening;

a seal specimen provided in said opening and providing a sealing engagement surrounding said shaft;

a contaminant contained in the canister enclosure and directed onto said shaft and seal specimen within said enclosure; and an actuator assembly connected directly to the shaft and actively imparting controlled displacements to the shaft to simulate changes in axial and lateral displacements applied to said shaft during operation of the rotary seal test machine.

7. The rotary seal test machine according to claim 6, wherein said actuator assembly includes a controller programmed to dynamically simulate axial and lateral forces experienced during real world driving of a vehicle.

* * * * *